US008477989B2

(12) United States Patent
Bresolin

(10) Patent No.: US 8,477,989 B2
(45) Date of Patent: Jul. 2, 2013

(54) METHOD OF TAKING AN IMAGE OF AN OBJECT RESIDING IN A TRANSPARENT, COLORED CONTAINER

(75) Inventor: Stefano Bresolin, Durham, NC (US)

(73) Assignee: Parata Systems, LLC, Durham, NC (US)

(*) Notice: Subject to any disclaimer, the term of this patent is extended or adjusted under 35 U.S.C. 154(b) by 841 days.

(21) Appl. No.: 12/687,356

(22) Filed: Jan. 14, 2010

(65) Prior Publication Data

US 2011/0170764 A1 Jul. 14, 2011

(51) Int. Cl.
*G06K 9/00* (2006.01)
(52) U.S. Cl.
USPC ............................. 382/100; 382/142; 348/127
(58) Field of Classification Search
USPC 382/100, 128, 142, 143; 348/127; 250/223 B
See application file for complete search history.

(56) References Cited

U.S. PATENT DOCUMENTS

| 5,502,559 | A | 3/1996 | Powell et al. |
| 6,535,637 | B1 | 3/2003 | Wootton et al. |
| 6,771,369 | B2 | 8/2004 | Rzasa et al. |
| 7,028,723 | B1 | 4/2006 | Alouani et al. |
| 7,218,395 | B2 * | 5/2007 | Kaye et al. ............. 356/301 |
| 7,317,393 | B2 * | 1/2008 | Maloney ............. 340/568.1 |
| 2004/0183237 | A1 | 9/2004 | McGrath et al. |
| 2005/0134856 | A1 | 6/2005 | Rutledge |
| 2008/0183410 | A1 | 7/2008 | Klein et al. |
| 2009/0080735 | A1 * | 3/2009 | Chapman et al. ............. 382/128 |
| 2010/0128165 | A1 | 5/2010 | Newcomb et al. |

FOREIGN PATENT DOCUMENTS

| CN | 101118363 A | 6/2008 |
| EP | 1 003 027 A1 | 5/2000 |
| WO | WO00/06078 | 2/2000 |

OTHER PUBLICATIONS

The International Search Report and the Written Opinion for International Application No. PCT/US2009/057383, mailed Dec. 7, 2009.
The International Search Report and Written Opinion of PCT/US2010/059373 mailed Feb. 22, 2011.
International Preliminary Report of Patentability of PCT/US2010/059373, mailed Jul. 26, 2012.

* cited by examiner

*Primary Examiner* — Gerald J. O'Connor
*Assistant Examiner* — John Go
(74) *Attorney, Agent, or Firm* — Myers Bigel Sibley & Sajovec, P.A.

(57) ABSTRACT

A method of acquiring an image of a pharmaceutical in a colored, transparent pharmaceutical vial includes the steps of: providing a generally cylindrical, colored, transparent pharmaceutical vial having a closed lower end, the lower end having a radially outward lower section, a radially inward upper section, and a transition section that merges with the upper and lower sections; identifying the transition section of the vial with a vision system; detecting the color of the transition section; illuminating the vial; acquiring an image of the vial and pharmaceutical; and adjusting the colors of the image based on the color of the transition section. In some embodiments, the method further comprises the step of comparing the image to a pre-stored image of an expected pharmaceutical to determine whether the identity of the pharmaceutical in the vial matches the identity of the expected pharmaceutical. This method can improve the reliability and consistency of the images produced.

18 Claims, 10 Drawing Sheets

METHOD OF TAKING AN IMAGE OF AN OBJECT RESIDING IN A TRANSPARENT, COLORED CONTAINER

FIELD OF THE INVENTION

The present invention is directed generally to imaging, and more particularly to imaging of an object within a container.

BACKGROUND OF THE INVENTION

There is an ongoing and predicted long-term shortage of licensed pharmacists. Due to the increasing age of the population and the ever-increasing number of prescription medicines available, the demand for prescription drugs is growing at rate that will far exceed the capacity and numbers of licensed pharmacists. The net impact of this imbalance is that pharmacists are increasingly spending more time doing clerical and administrative tasks such as verifying filled prescriptions and checking data entry done by pharmacy technicians. Since the capacity of any one pharmacist is fixed, the output of a pharmacy has become constrained. Consequently, the labor and total cost per prescription continues to rise. The December 2000 Department of Health and Human Services Report to Congress titled "The Pharmacist Workforce: A Study of the Supply and Demand for Pharmacists", which is hereby incorporated by reference into the present application, provides an overview of the above problem.

Due to these increased demands on a pharmacist's time, and the resulting increased reliance on technicians and other non-professional staff to fill prescriptions, there is an increased chance for prescription error. While these errors may take many forms, the likelihood of a dangerous or life threatening "adverse drug event" increases proportionally with the increased chance of prescription fill error. Several studies have shown that prescription error rates are consistently in the 2% to 7% range, with a 4% error rate often cited as a reliable average. The number of deaths due to medication errors is estimated to exceed 7,000 per year in the United States alone. Of course, this number does not include non-fatal conditions from drugs that also result in some form of trauma or injury. The resulting litigation costs associated with these prescription fill errors have also dramatically increased.

Many existing pharmacy filling systems and procedures still require a human operator, whether that operator is a technician or a licensed pharmacist, to validate visually whether the drug that is delivered to the customer is correct. Thus, the human factor can contribute to the majority of prescription fill errors. Existing visual verification techniques typically rely on comparing an electronic image of the prescribed medication, i.e., a picture of the prescribed medication retrieved from a data library, with the actual medication that is dispensed for the patient. Other systems and procedures rely on comparing the dispensed medication with that in the original manufacturer's supply container, or comparing an electronic image of the filled prescription with an electronic image of the prescribed medication retrieved from a data library.

Each of these verification systems present similar problems. First, these known verification methods assume that all drugs are visually distinct. This assumption causes many problems because many drugs are not, in fact, visually distinct and, in other cases, the visual differences between drugs is very subtle. For instance, manufacturers are rapidly running out of unique shapes, colors and sizes for their solid dosage form products. To further complicate the problem, generic drug manufactures may be using shapes, colors, and sizes that are different than that of the original manufacturer. Second, even though some known systems may utilize a National Drug Code (NDC) bar code to verify that the supply bottle being accessed corresponds correctly to the patient's prescription, a fraction of filled prescriptions that are never picked up are returned to the supply shelves for reuse in later prescriptions. These reused bottles will not, therefore, have a manufacturer's bar code on them. It is, therefore, difficult, if not impossible, to incorporate such validation schemes for these unused prescriptions. Furthermore, in these circumstances, a supply bottle is not available for a visual comparison with the filled prescription. Finally, each of these known manual verification and validation techniques typically requires that the pharmacist spend a significant portion of his day performing these administrative or clerical tasks and allows less time for patient consultation and other professional pharmacist activities.

Solid dosage pharmaceuticals (e.g. pills, tablets, and capsules) each have a unique chemical composition associated with them. This is often referred to as a chemical signature or fingerprint. Pharmaceuticals with varying dosage levels of the same active ingredient may have unique chemical signatures as well. Even slight variations in the active ingredient typically produce a unique chemical signature. In that regard, most pharmaceuticals can be identified accurately by the use of some form of chemical analysis. This same methodology may be applied to other forms of medication (e.g. liquids, creams, and powders). Particularly with solid dosage pharmaceutical products, while a group or package of products may look identical in the visible portion of the spectrum each product may have a unique chemical signature in the near-infrared wavelength range (800 to 2500 nm). For example, U.S. Pat. No. 6,771,369 to Rzasa et al. describes a pharmaceutical discrimination system that relies on NIR for scanning the contents of a pharmaceutical vial. As another example, U.S. Pat. No. 7,218,395 to Kaye et al. describes the use of Raman spectroscopy for scanning vial contents. U.S. Patent Publication No. 20080183410 describes another spectroscopy-based discrimination system that can analyze pharmaceuticals as they are present in a capped pharmaceutical vial.

Although these spectroscopy systems can be very accurate, in many instances it may be necessary or helpful to verify the identity of the pharmaceutical visually. Naturally, if the pharmaceutical has already been dispensed into a vial, removal from the vial (or even uncapping of the vial) can slow the dispensing process. However, it is common for pharmaceutical vials to be largely transparent and have an amber color. The use of amber-colored vials began as an attempt to preserve the potency of the pharmaceuticals contained therein (based on the belief that amber coloration helped to prevent the passage of UV radiation, which might damage the pharmaceuticals), and their use has continued as a matter of convention. Thus, the use of a conventional vision system to verify the contents of a vial visually is difficult, because often the color of the pharmaceutical is one of its most distinguishing characteristics, and the amber color of the vial can adversely affect the accuracy of the color presented to the vision system.

It may be desirable to provide a vision system that can accurately detect pharmaceuticals, including their color, while inside a capped pharmaceutical vial. One proposed approach is described in U.S. patent application Ser. No. 12/249,402, filed Oct. 10, 2008, the disclosure of which is hereby incorporated by reference herein. In the proposed system, a vial filled with tablets is illuminated with light that is the "reverse" color of the vial (in terms of RGB values or the like). This approach has been shown to allow more accurate viewing of the tablets within the vial. However, in order for this approach to be effective, the color of the vial should be accurately assessed, and the variance in color between vials of different manufacturers, different lots, different sizes, and the like can be considerable. Consequently, it may be desirable to provide a technique for assessing the color of a vial that is reproducible from vial to vial in order to accurately and reliably assess the contents of the vial.

SUMMARY OF THE INVENTION

As a first aspect, embodiments of the present invention are directed to a method of acquiring an image of a pharmaceutical in a colored, transparent pharmaceutical vial. The method comprises the steps of: providing a generally cylindrical, colored, transparent pharmaceutical vial having a closed lower end, the lower end having a radially outward lower section, a radially inward upper section, and a transition section that merges with the upper and lower sections; identifying the transition section of the vial with a vision system; detecting the color of the transition section; illuminating the vial; acquiring an image of the vial and pharmaceutical; and adjusting the colors of the image based on the color of the transition section. In some embodiments, the method further comprises the step of comparing the image to a pre-stored image of an expected pharmaceutical to determine whether the identity of the pharmaceutical in the vial matches the identity of the expected pharmaceutical. This method can improve the reliability and consistency of the images produced.

As a second aspect, embodiments of the present invention are directed to a method of acquiring an image of a pharmaceutical in a colored, transparent pharmaceutical vial, comprising the steps of: providing a generally cylindrical, colored, transparent pharmaceutical vial having a closed lower end, the lower end having a radially outward lower section, a radially inward upper section, and a transition section that merges with the upper and lower sections; identifying the transition section of the vial with a vision system; detecting the color of the transition section; illuminating the vial with colored light, wherein the color of the light is selected responsive to the detecting step; and acquiring an image of the vial and pharmaceutical.

DETAILED DESCRIPTION OF EMBODIMENTS OF THE INVENTION

Figure 1:
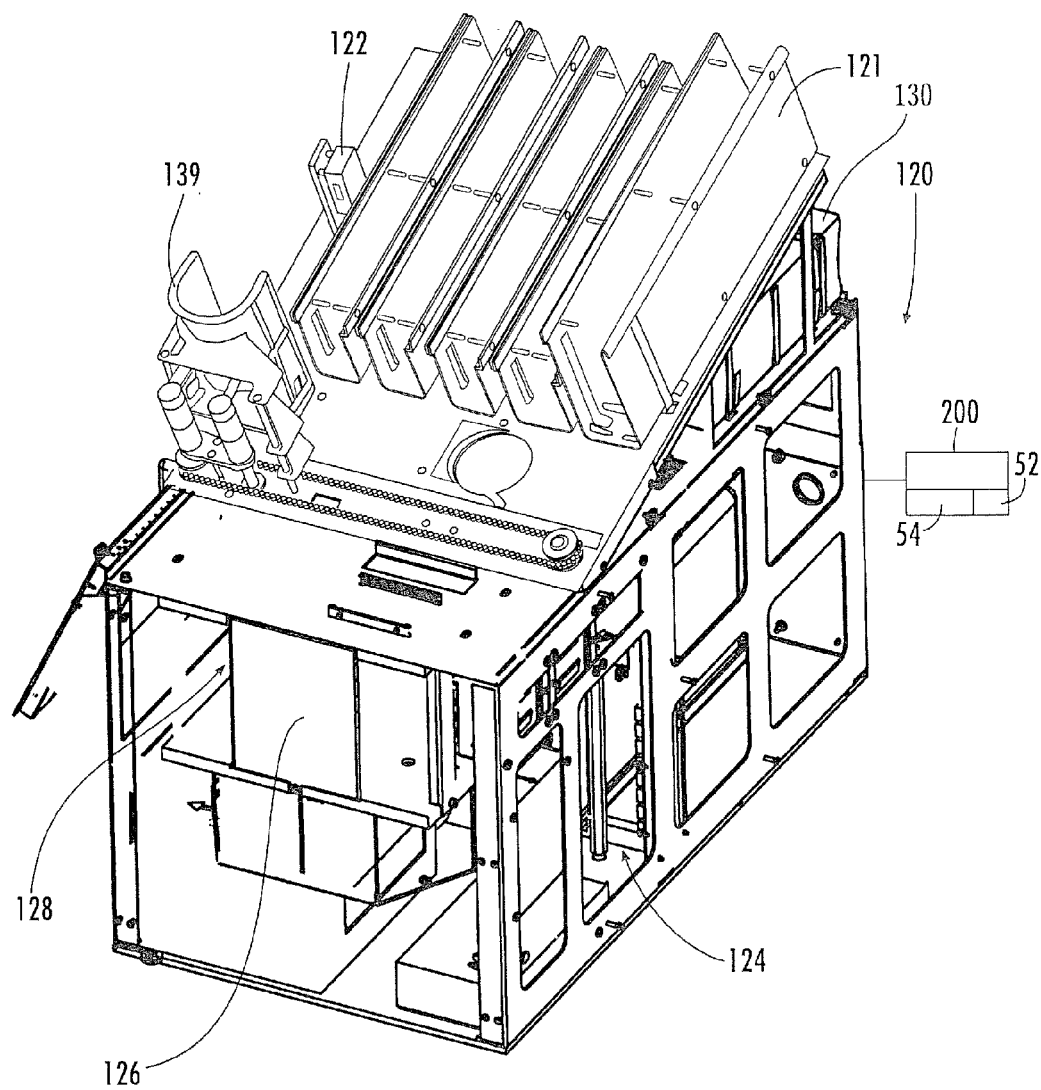
FIG. 1 is a perspective view of a system suitable for performing methods according to embodiments of the present invention.

The present invention will now be described more fully hereinafter, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout. Thicknesses and dimensions of some components may be exaggerated for clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the expression "and/or" includes any and all combinations of one or more of the associated listed items.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

Well-known functions or constructions may not be described in detail for brevity and/or clarity.

Turning now to the figures, FIG. 1 illustrates a pharmaceutical verification system 120 according to embodiments of the present invention. The system 120 includes a vial loading station 121, bar code scanning or RFID reading station 122, a vision station 124, a spectroscopy station 126, a stamping station 128, and an offload station 130 located underneath the vial loading station 121. Vials are moved between these stations with a sliding conveyor 139 adjacent the bar code scanning station and a wheel conveyor (not shown in FIG. 1—see FIG. 4). A controller 200 controls the operation of the various stations and the conveyor. The operation of the system 120 is described in greater detail in co-assigned U.S. Provisional Patent Application Ser. No. 61/118,006, filed Nov. 26, 2008, and U.S. patent application Ser. No. 12/623,917, the disclosure of each of which is hereby incorporated herein in its entirety.

Figure 2:
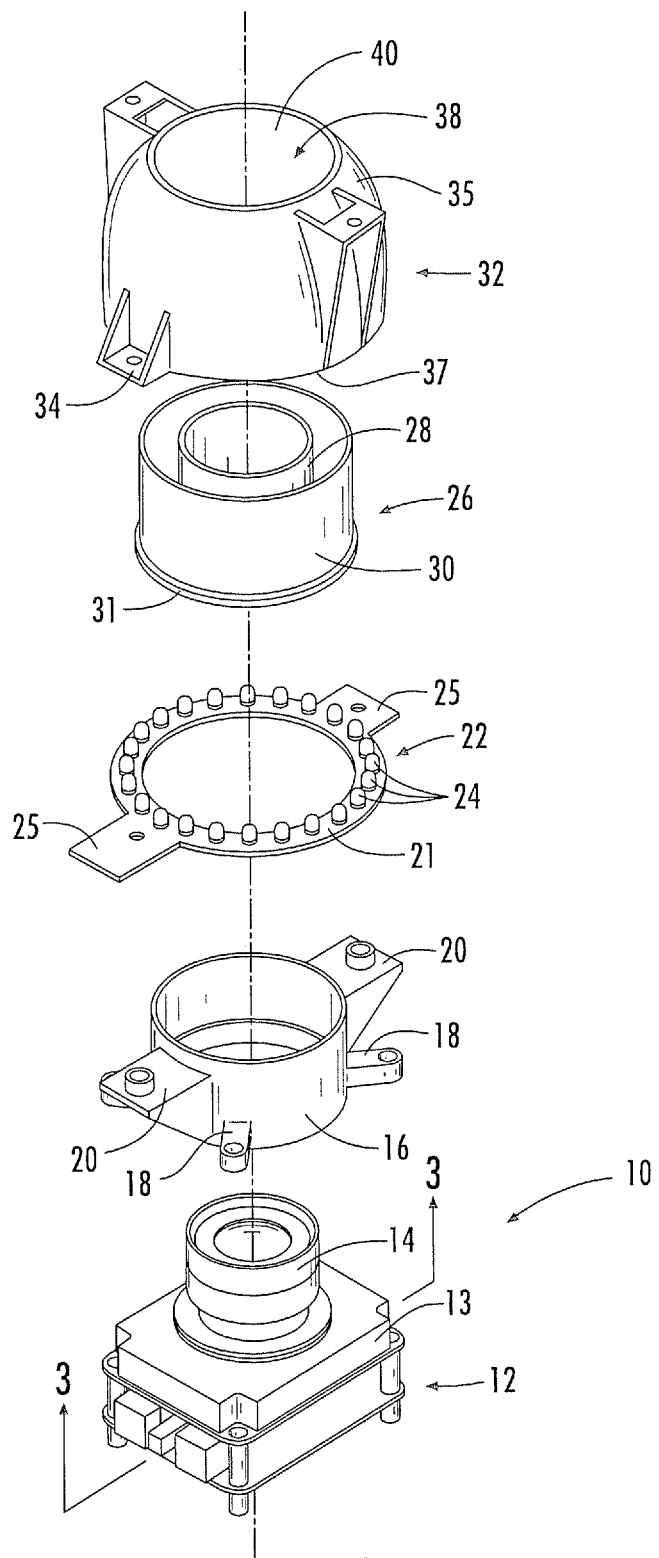
FIG. 2 is an exploded perspective view of components of a vision system include in the overall system of FIG. 1.
Figure 3:
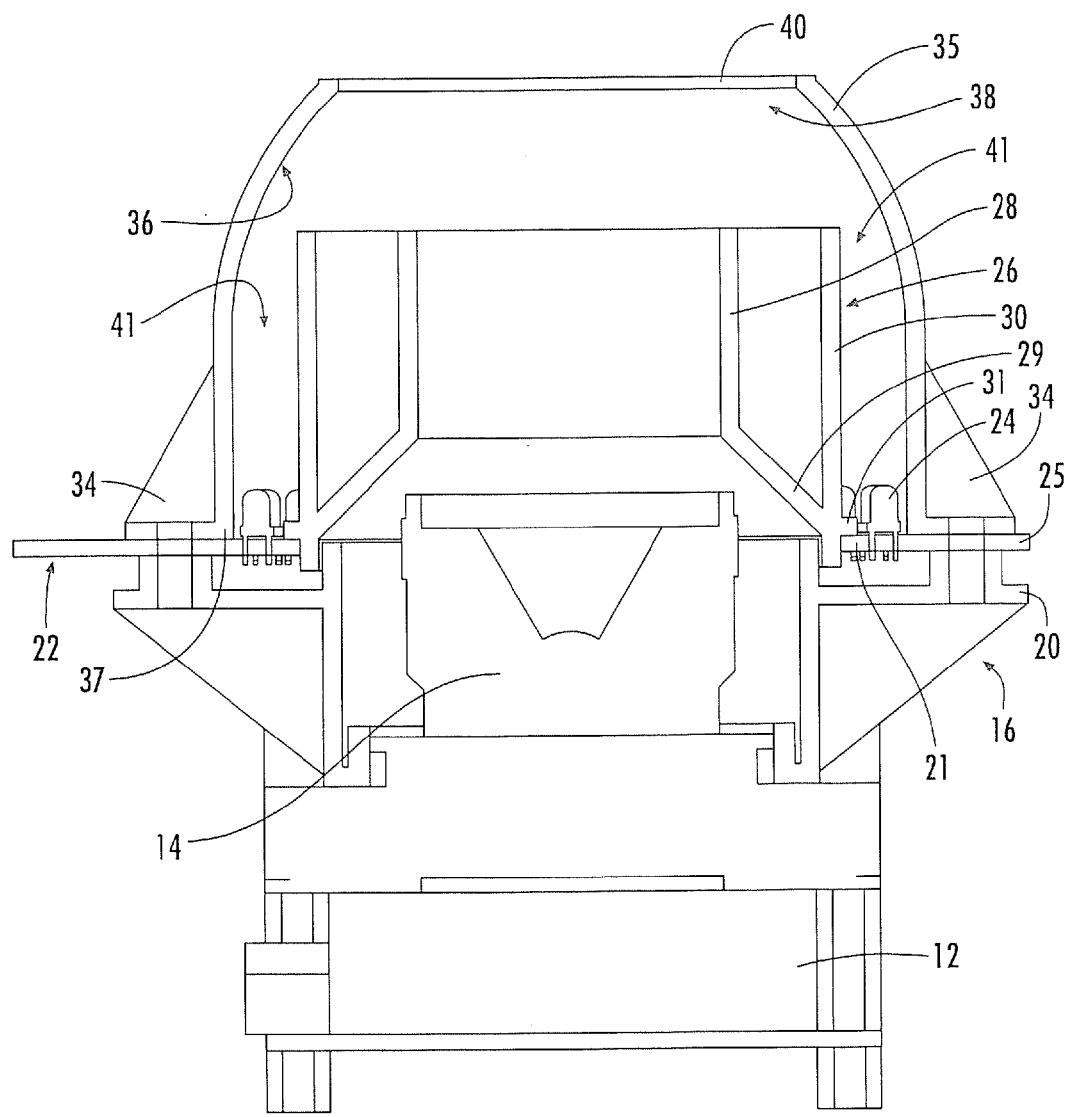
FIG. 3 is a section view of the components of FIG. 2 in an assembled form taken along lines 3-3 of FIG. 2.

Turning now to FIGS. 2 and 3, an imaging system for use in the vision station 124, designated broadly at 10, is shown therein. The imaging system 10 includes a camera 12, a light ring 22, a light curtain 26, and a light dome 32. Each of these components is described in greater detail below and in U.S. patent application Ser. No. 12/623,878, the disclosure of which is hereby incorporated herein in its entirety.

The camera 12 can be any camera that is suitable for the acquisition of digital images. An exemplary camera 12 is Model No. Lw570C, available from Lumenera Corp., Ottawa, Canada. As shown in FIGS. 2 and 3, the camera 12 is oriented and mounted such that its lens 14 faces upwardly from its body 13. A sleeve 16 rests on the upper surface of the body 13 and circumferentially surrounds the lens 14. The sleeve 16 includes radially-extending tabs 18 that are used to mount the sleeve 16 to the camera 12, and also includes two flanges 20 that extend radially from diametrically opposed sections of the upper edge of the sleeve 16.

Referring still to FIGS. 2 and 3, the light ring 22 has a generally annular and planar body portion 21. Tabs 25 extend radially from diametrically opposed sections of the body portion 21 and are used to provide mounting locations for the light ring 22 on top of the sleeve 16. A series of light emitting diodes (LEDs) 24 are mounted on the upper surface of the body portion 21. The LEDs 24 are alternating red/green/blue (RGB) LEDs that emit different wavelengths of light using a conventional RGB color scheme or other color scheme to produce white light. The LEDs 24 are adjustable in intensity, such that the intensity of red, green and/or blue light can be varied. As such, the color of light emanating from the light ring 22 can be adjusted as desired. Intensity levels of red, green and blue light that can be employed to produce a particular shade of light are known to those of skill in this art and need not be detailed herein.

Referring again to FIGS. 2 and 3, the light curtain 26 includes an annular inner wall 28 and a concentric outer wall 30. A beveled surface 29 (FIG. 3) joins the lower edges of the inner and outer walls 28, 30. A radial lip 31 extends outwardly from the outer wall 30 and rests on the inner edge of the body portion 21 of the light ring 22. This placement of the lip 31 positions the outer wall 30 radially inward of the LEDs 24. The inner wall 28 is positioned above and generally axially aligned with the lens 14 of the camera 12.

Still referring to FIGS. 2 and 3, the light dome 32 is generally bowl-shaped, with a dome wall 35 having an opening 38 in its upper portion and a perimeter 37 at its lower edge. A clear glass window 40 fills the opening 38. Flanges 34 (only one of which is shown in FIG. 2) extend radially outwardly from diametrically opposed sections of the lower edge of the dome wall 35 and align with the flanges 20 of the sleeve 16 and the tabs 25 of the light ring 22. Fasteners can be inserted through the flanges 34, the tabs 25 and the flanges 20 to fasten the light dome 32, the light ring 22, and the sleeve 16 together.

Referring now to FIG. 3, the inner surface 36 of the dome wall 35 and the outer wall 30 of the light curtain 26 form an annular gap 41 through which light from the LEDs 24 can pass. The dome wall 35 has sufficient curvature that the edges of the window 40 are radially inward of the upper edges of the outer wall 30; as a result, light from the LEDs 24 cannot shine directly onto the window 40. Also, the inner surface 36 is typically formed of an anti-glare material or treated with an anti-glare coating (such as a flat black paint) to reduce or minimize specular reflection and/or increase or maximize diffuse reflection.

Figure 4:
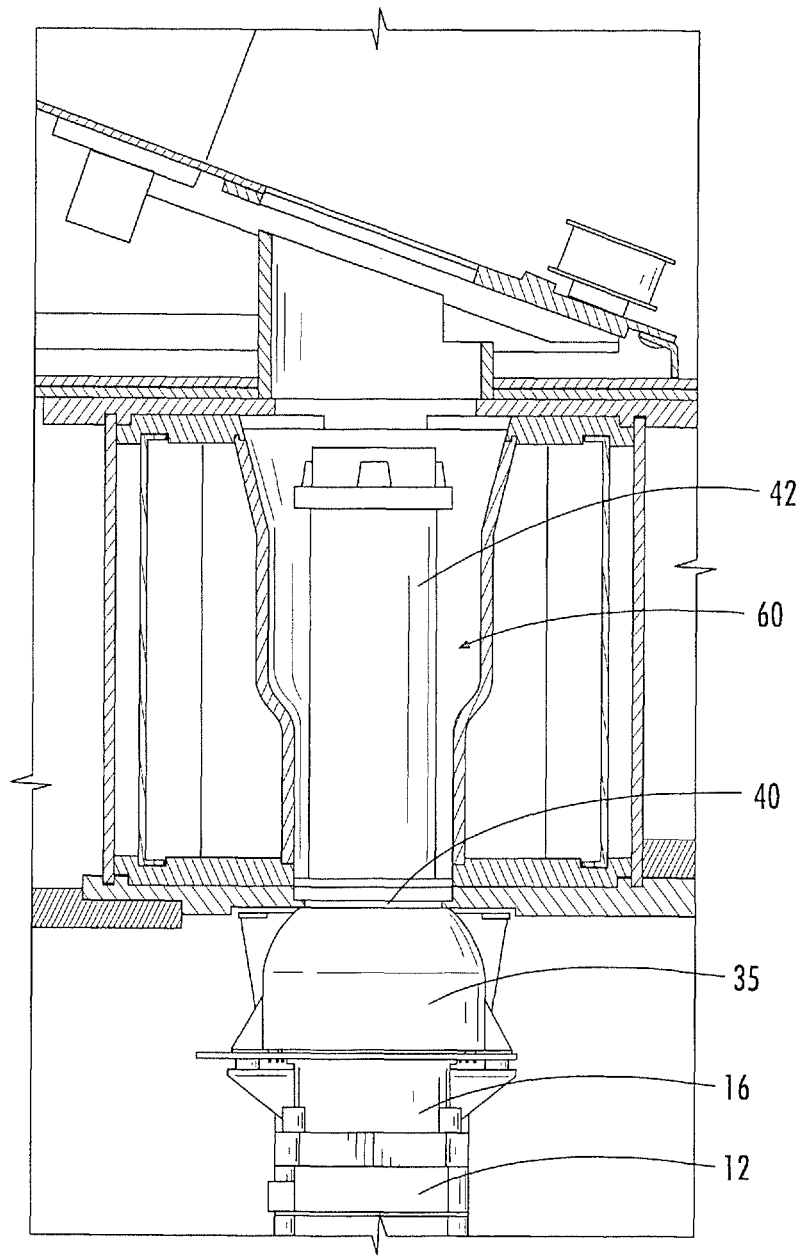
FIG. 4 is a section view of the vision system of FIG. 2 with a pharmaceutical vial residing therein.

Turning now to FIG. 4, the system 10 will ordinarily be employed with a chamber, such as chamber 60, in which resides the object (in this instance a pharmaceutical vial 42) for imaging. The chamber 60 is typically light-tight, such that the only appreciable light entering the chamber 60 enters through the window 40. In some embodiments, the chamber 60 will include a trap door or cover that allows the insertion of the object into the chamber but closes to prevent light from entering. In this embodiment, the walls of the chamber 60 are formed by the wheel conveyor 62 that conveys the vial 42 between stations of the system 120, but other configurations may also be suitable.

Referring back to FIG. 1, a controller 200 is connected to the camera 12 and the light ring 22. The controller 200 includes a memory 52 (which may be local or remote) that has stored image data for multiple pharmaceutical tablets. The stored image data may be in the form of images, and/or may include information on pill geometry, markings, scoring and the like. The controller 200 also has a processor 54 that enables an image taken by the camera 12 to be compared to the stored image data to determine whether one or more visual features or attributes of the dispensed pharmaceutical match a pharmaceutical stored in the memory 52.

In operation, as shown in FIG. 4 a vial 42 (typically a capped vial) containing a dispensed pharmaceutical is deposited in the chamber 60 and rests with its lower end on the window 40. The controller 200 activates the LEDs 24 of the light ring 22. Light from the LEDs 24 travels through the gap 41 to the inner surface 36 of the dome wall 35. However, because of the location of the outer wall 30 of the light curtain 26 and the position of the window 40, none of the light from the LED reaches the window 40 directly; instead, light reaching the window 40 (and, in turn, the vial 42 and the tablets residing therein) is indirect light, which produces little to no glare. This indirect light illuminates the vial 42 and tablets sufficiently for an image to be taken with the camera 12. The controller 200 then stores the image for subsequent processing, comparison to a known image, and/or other tasks.

Figure 5:
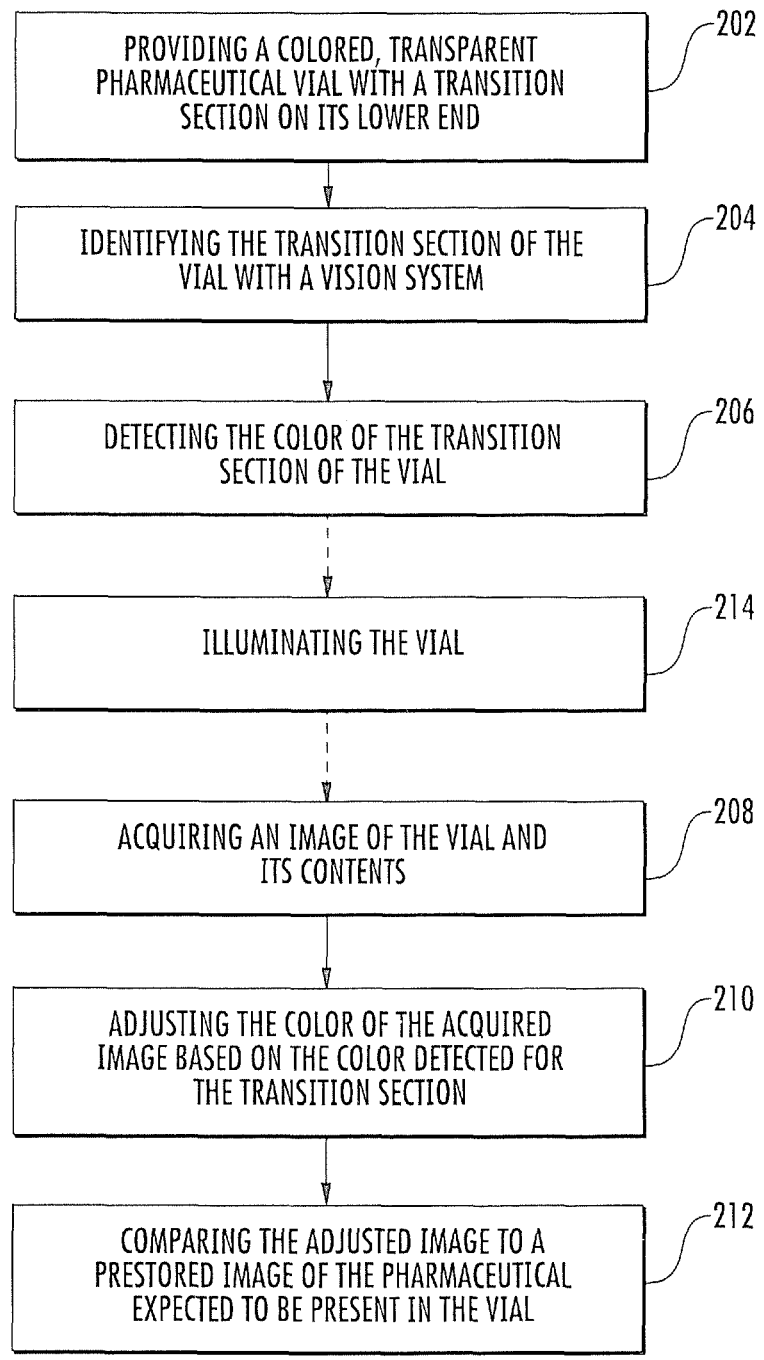
FIG. 5 is a flow chart describing operations associated with a method according to embodiments of the present invention.
Figure 6:
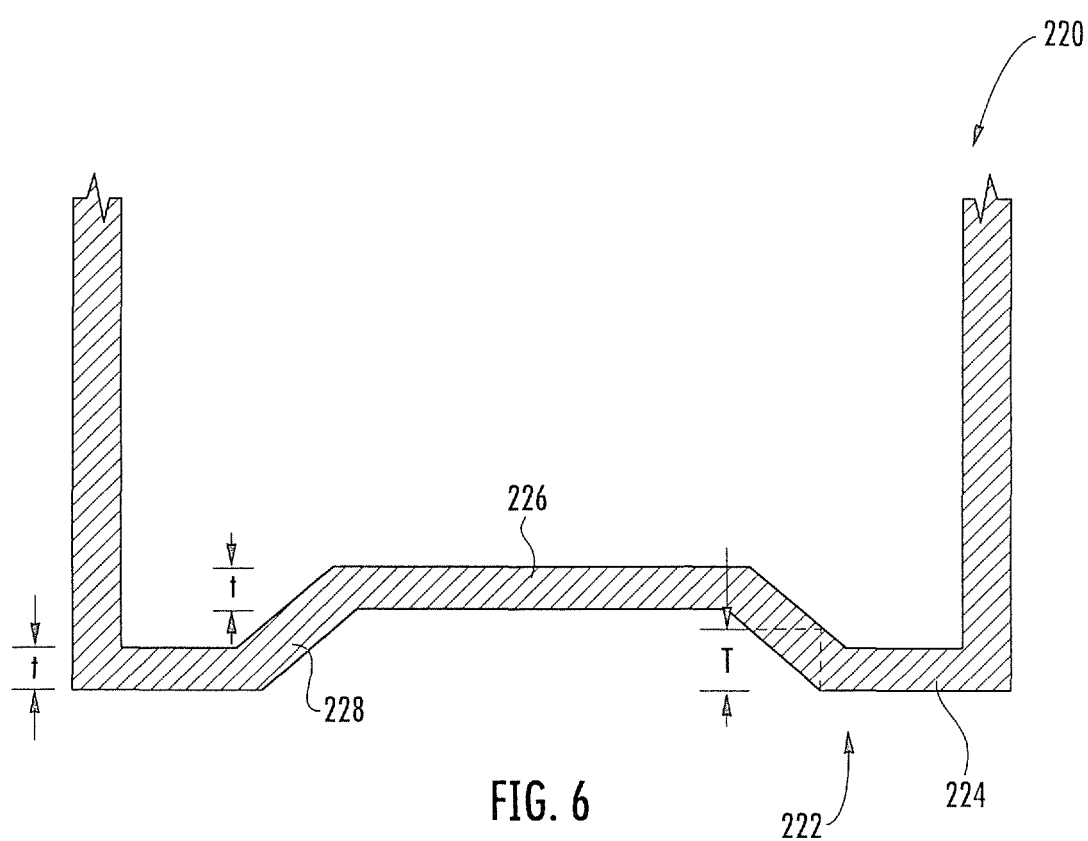
FIG. 6 is a greatly enlarged perspective view of the lower end of a pharmaceutical vial.
Figure 7A:
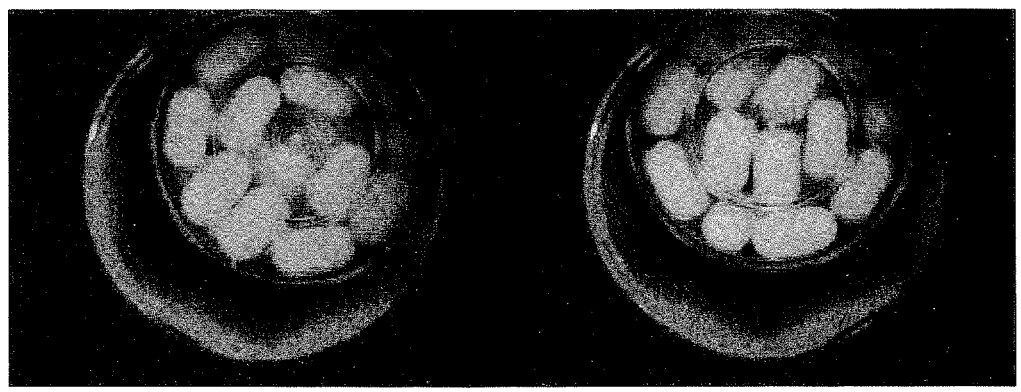
FIGS. 7A and 7B are images of two vials containing white plastic artificial pills, wherein the image of FIG. 7A is not adjusted according to methods of the present invention and the image of FIG. 7B is adjusted.
Figure 7B:
Figure 8A:
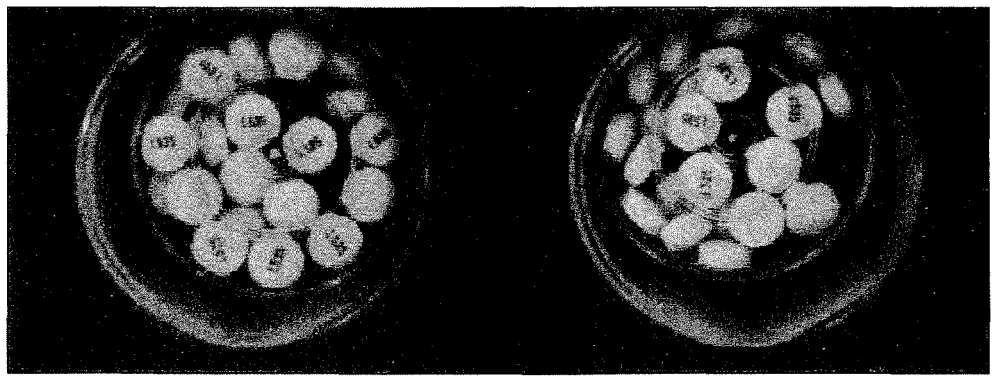
FIGS. 8A and 8B are images of two vials containing yellow baby aspirin, wherein the image of FIG. 8A is not adjusted according to methods of the present invention and the image of FIG. 8B is adjusted.
Figure 8B:
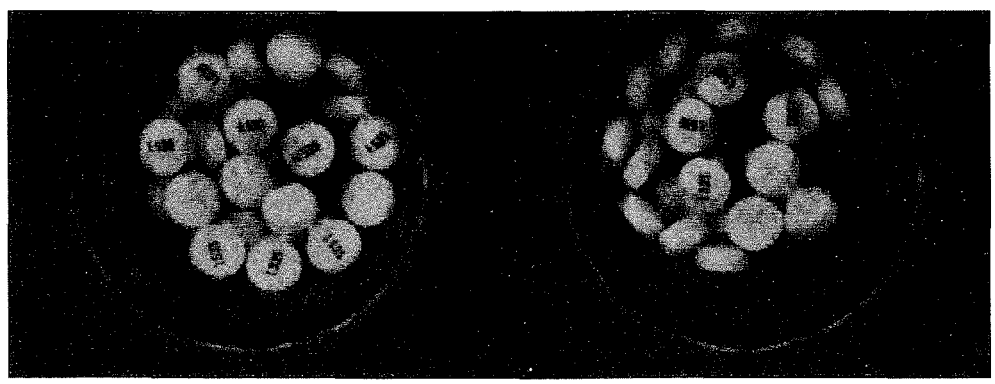

The system of FIGS. 2-4 can be employed to practice embodiments of methods according to the present invention. Such an embodiment is illustrated in FIG. 5. The method commences with the provision of a pharmaceutical vial (Block 202). The lower end 222 of a typical vial 220 is illustrated in FIG. 6. The vial 220 is typically generally cylindrical (although other shapes, e.g., square or rectangular, may be used) and closed at its lower end 222. The lower end 222 has a radially outward lower section 224, a radially inward upper section 226, and a substantially annular transition section 228 that merges with the lower section 224 and the upper section 226. The nominal wall thickness of the lower end 222 is generally between about 0.035 and 0.045 inches and is the same for each of the lower, transition and upper sections 224, 228, 226; because the transition section 228 is canted at an oblique angle to the lower and upper sections 224, 226, the dimension T of the transition section 228 perpendicular to the lower and upper sections 224, 226 is greater than the thickness t of the lower and upper sections 224, 226. The outer diameter of the vial 220 is typically between about 1.25 and 1.925 inches.

Returning to FIG. 5, a vision system (such as that described above) is used to identify the transition section 228 of the vial 220 (Block 204), which is typically the center of the vial 220. The vision system 10 and/or the controller 200 then determine the color of the transition section 228 (Block 206). It has been discovered that the transition section 228 of the lower end of the vial 220 (perhaps due to the greater thickness T it presents for imaging from a vantage point beneath the lower end of the vial 220) provides a more representative color for the vial 220 than the remaining visible portions of the vial 220. Identification of the transition section 228 can be achieved in a number of ways, including geometric identification of the center of the vial 220.

The vision system then acquires an image of the vial 220 and its pharmaceutical contents (Block 208); in some embodiments, the vial 220 may be illuminated as the image is acquired (Block 214). After the image is acquired, the colors of the image, and in particular the pharmaceuticals contained in the vial 220, are adjusted responsive to the color of the transition section 228 determined in Block 206 (Block 210). The adjustment of the image is intended to cause the images of tablets from different vials to appear similar. As stated above, the transition section 228 can provide a particularly accurate representative color for the vial 220, such that adjustment of the image based on the color of the transition section 228 can enable the images of the same tablets in different vials to appear the same in the adjusted images.

Subsequently, the adjusted image is compared to a pre-stored image of the expected contents of the vial 200 to determine if the vial 220 contains the expected contents (Block 212). (The expected contents are typically determined via the scanning of a bar code on the vial 220 the bar code scanning station 122, but can also be determined manually or in another automated manner). As discussed above, vials can vary in color from lot to lot and manufacturer to manufacturer. As a result, tablets contained within different vials can appear differently to a camera acquiring images thereof. Because the image of the vial 220 has been adjusted based on the color of the transition section 228 of the vial 220, the comparison of the vial/tablet image with a pre-stored image of the tablets in a vial can be more accurate and reliable.

Figure 9A:
FIGS. 9A and 9B are images of two vials containing green plastic artificial pills, wherein the image of FIG. 9A is not adjusted according to methods of the present invention and the image of FIG. 9B is adjusted.
Figure 9B:

FIGS. 7A-9B show images of pairs of vials with pharmaceutical tablets contained therein. Each pair of vials contains a plurality of tablets of the same pharmaceutical: the vials of FIGS. 7A and 7B contain white plastic artificial pills; the vials of FIGS. 8A and 8B contain yellow baby aspirin; and the vials of FIGS. 9A and 9B contain green plastic artificial pills. In the unadjusted images of FIGS. 7A, 8A and 9A, it can be seen that tablets of the same pharmaceutical in different vials appear somewhat different, which can make a comparison of the images to a pre-stored standard image somewhat unreliable. The adjusted images of FIGS. 7B, 8B and 9B show that, after adjustment of the image based on the color of the transition section 228 of the vial 220, the appearance of the same tablets in the different vials is much more similar, thereby making a comparison to a standard pre-stored image more reliable.

It should be noted that, due to the adjustable nature of the LEDs 24 of the light ring 22, the color of light illuminating the vial 42 and tablets can be selected for advantageous imaging. For example, as discussed in co-pending and co-assigned U.S. patent application Ser. No. 12/249,402, filed Oct. 10, 2008, the disclosure of which is hereby incorporated herein by reference, images of tablets contained in a transparent amber-colored vial and acquired through the wall of the vial may exhibit substantially the same color as the tablets themselves when the vial is illuminated with light of a "reverse" color. As discussed in detail in the cited patent application, a "reverse" color is one that uses reciprocal values for red, green and blue in an RGB system. The use of light that is the reverse color of a transparent amber vial (e.g., a bluish hue for an amber vial) can enable images of objects in the vial, wherein the images are acquired through the walls of the vial, to exhibit the same color as the objects would exhibit without the vial. Thus, the LEDs 24 of the light ring 22 can be adjusted to produce light having a "reverse" color to that of the vial (again, as an example, a bluish light for an amber-colored vial).

Figure 10:
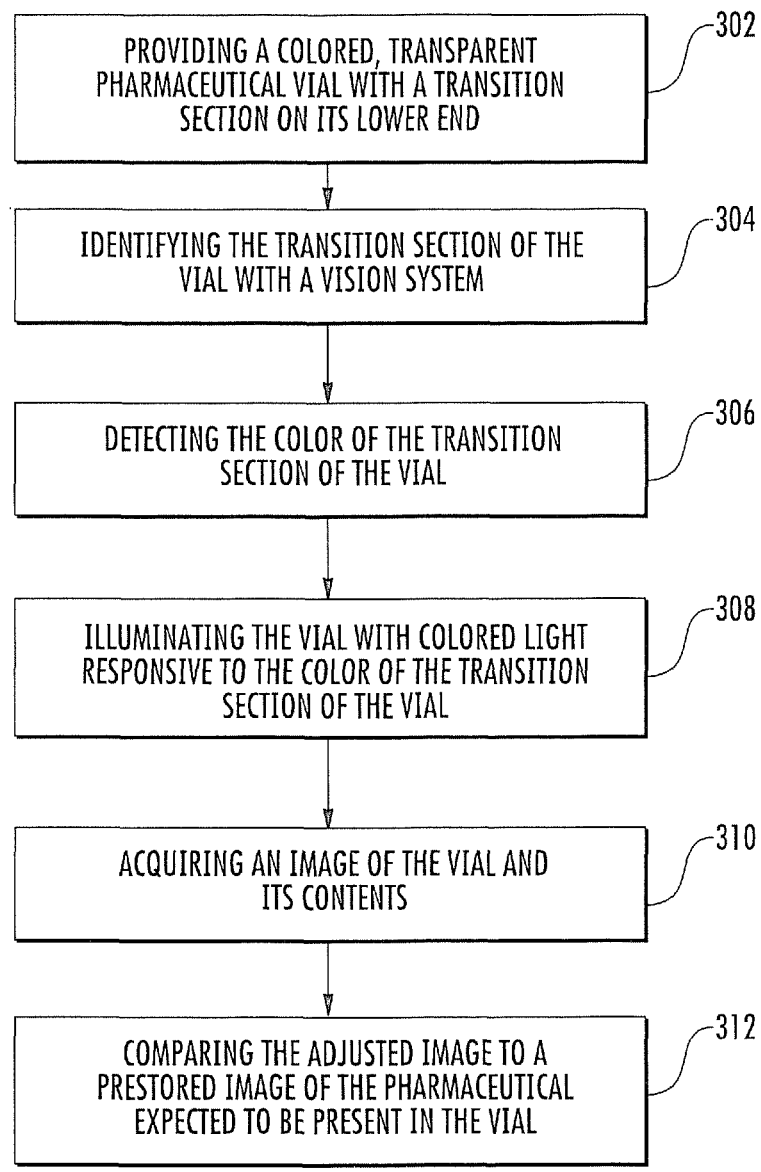
FIG. 10 is a flow chart describing operations associated with a method according to alternative embodiments of the present invention.

This capability can be combined with the benefits described above in conjunction with the detection of the color of the transition section 228 of a vial 220. Turning now to FIG. 10, an alternative method commences with the provision of a pharmaceutical vial as described above (Block 302), the identification of a transition section in the vial (Block 304), and the determination of the color of the transition section (Block 306). The method continues with the illumination of the vial and its contents, wherein the color of the illuminating light is selected based on the color of the transition section 228 determined at Block 306 (Block 308). An image of the vial and its contents is then acquired (Block 310). The image of the vial is compared to a pre-stored image of the expected contents of the vial to determine whether the identity of the contents matches the identity of the expected contents (Block 312).

As discussed above, in some embodiments, the color selected for illumination may be substantially the reverse of the color of the vial 220. In one embodiment, the color of the vial 220 can be determined by first taking an image of the vial 42 with the camera 12. A histogram of that image can be produced. The inverse color of the histogram can then be determined, and the controller 200 can, through the LEDs 24 of the light ring 22, generate light of the inverse color. In other embodiments, a sensor (not shown) may be included in the vision system 10 to detect the color of the vial 42. The sensor can transmit signals regarding the color of the vial 42 to the controller 200, which then induces the LEDs 24 of the light ring 22 to produce light of a "reverse" color to that of the vial 42. In such an embodiment, the system 10 can "tune" the light emitted from the LEDs 24 to account for differently-colored vials or variations in color due to different manufacturers, different lots, or the like. Another scenario involves setting the light ring to a particular RGB setting for a particular color vial (e.g., amber) and using that color for all images, then using this method to fine tune the final image to account for possible lot to lot variations.

Also, in some embodiments, the controller 200 may, in view of the identity of the prescribed pharmaceutical labeled on the vial (typically in bar code form), adjust the light produced by the LEDs 24 of the light ring 22 to a color that is particularly advantageous for distinguishing the prescribed pharmaceutical from a similar pharmaceutical. Thus, in those embodiments the color of the light may be one that is not substantially the reverse color of the vial, but is advantageous for detection of the particular pharmaceutical in the particular vial by most greatly enhancing the differences from the similar pharmaceutical. In any event, detection of the color of the transition section can improve the image produced for comparison to the pre-stored image of the tablets.

Those skilled in this art will appreciate that color schemes other than RGB may be employed. In addition, in some embodiments electromagnetic radiation outside of the visible light range, such as ultraviolet or infrared, may also be employed.

The foregoing is illustrative of the present invention and is not to be construed as limiting thereof. Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. The following claims are provided to ensure that the present application meets all statutory requirements as a priority application in all jurisdictions and shall not be construed as setting forth the scope of the invention.

That which is claimed is:

1. A method of acquiring an image of a pharmaceutical in a colored, transparent pharmaceutical vial, comprising the steps of:
    providing a generally cylindrical, colored, transparent pharmaceutical vial having a closed lower end, the lower end having a radially outward lower section, a radially inward upper section, and a transition section that merges with the upper and lower sections;
    identifying the transition section of the vial with a vision system;
    detecting the color of the transition section;
    illuminating the vial;
    acquiring an image of the vial and pharmaceutical; and
    adjusting the colors of the image based on the color of the transition section.

2. The method defined in claim 1, wherein the pharmaceutical in the vial comprises a plurality of pharmaceutical tablets.

3. The method defined in claim 1, wherein the vial is an amber color, and the illuminating step comprises illuminating the vial with light of a bluish hue.

4. The method defined in claim 1, wherein nominal wall thicknesses of the lower, upper and transition sections of the vial are substantially the same.

5. The method defined in claim 1, wherein the transition section is substantially annular.

6. The method defined in claim 1, wherein the lower section of the vial has an outer diameter of between about 1.25 and 1.95 inches.

7. The method defined in claim 1, wherein the step of illuminating the vial comprises illuminating the vial with light that is substantially the reverse RGB color of the vial.

8. The method defined in claim 1, wherein, in cross-section, the transition section defines an oblique angle to the lower and upper sections.

9. The method defined in claim 1, further comprising comparing the image to a pre-stored image of an expected pharmaceutical to determine whether the identity of the pharmaceutical in the vial matches the identity of the expected pharmaceutical.

10. The method defined in claim 1, wherein the lower section of the vial has an outer diameter of between about 1.25 and 1.95 inches.

11. A method of acquiring an image of a pharmaceutical in a colored, transparent pharmaceutical vial, comprising the steps of:
    providing a generally cylindrical, colored, transparent pharmaceutical vial having a closed lower end, the lower end having a radially outward lower section, a radially inward upper section, and a transition section that merges with the upper and lower sections;
    identifying the transition section of the vial with a vision system;
    detecting the color of the transition section;
    illuminating the vial with colored light, wherein the color of the light is selected responsive to the detecting step; and
    acquiring an image of the vial and pharmaceutical.

12. The method defined in claim 11, wherein the pharmaceutical in the vial comprises a plurality of pharmaceutical tablets.

13. The method defined in claim 11, wherein the vial is an amber color, and the illuminating step comprises illuminating the vial with light of a bluish hue.

14. The method defined in claim 11, wherein nominal wall thicknesses of the lower, upper and transition sections of the vial are substantially the same.

15. The method defined in claim 11, wherein the transition section is substantially annular.

16. The method defined in claim 11, wherein the step of illuminating the vial comprises illuminating the vial with light that is substantially the reverse RGB color of the vial.

17. The method defined in claim 11, wherein, in cross-section, the transition section defines an oblique angle to the lower and upper sections.

18. The method defined in claim 11, further comprising comparing the image to a pre-stored image of an expected pharmaceutical to determine whether the identity of the pharmaceutical in the vial matches the identity of the expected pharmaceutical.

* * * * *